United States Patent [19]

Amoils

[11] Patent Number: 4,660,947
[45] Date of Patent: Apr. 28, 1987

[54] METHODS AND APPARATUS FOR USE IN OCULAR SURGERY

[76] Inventor: Selig P. Amoils, 90 Protea Avenue, Athol, Johannesburg, South Africa

[21] Appl. No.: 639,993

[22] Filed: Aug. 13, 1984

[30] Foreign Application Priority Data

Aug. 11, 1983 [ZA] South Africa ...................... 83/5888
Oct. 28, 1983 [ZA] South Africa ...................... 83/8042

[51] Int. Cl.$^4$ .............................................. A61B 3/10
[52] U.S. Cl. ..................................... 351/212; 351/247
[58] Field of Search ................ 351/212, 211, 221, 247

[56] References Cited

U.S. PATENT DOCUMENTS 4,046,463 9/1977 La Russa et al. .................... 351/212

Primary Examiner—Rodney B. Bovernick
Assistant Examiner—P. M. Dzierzynski
Attorney, Agent, or Firm—Rines and Rines; Shapiro and Shapiro

[57] ABSTRACT

Apparatus and method for use in ocular surgery to enable the surgeon to determine the degree of self correcting astigmatism to apply to the eye during the suturing procedure. The apparatus comprises an ocular microscope provided with a device for directing a ring of light onto the anterior surface of the cornea of the eye such that the cornea will reflect the ring for viewing in the eyepiece of the microscope. The eyepiece is provided with means for determining the shape of the reflected ring and hence the degree of astigmatism applied to the cornea by the surgeon. In particular this means may be in form of a comparison ring which may be viewed in the same field of view as the reflected ring and being adjustable by the surgeon to provide a series of comparison rings for comparison with the reflected ring and corresponding to successive degrees of corneal astigmatism.

5 Claims, 8 Drawing Figures

METHODS AND APPARATUS FOR USE IN OCULAR SURGERY

FIELD OF THE INVENTION

The present invention relates to method and apparatus for use in ocular surgery and particularly to an ocular microscope and methods for its use in surgical operations on a cataract infected eye involving the insertion of an artificial lens.

BACKGROUND OF THE INVENTION

In ocular surgery such as cataract surgery, corneal surgery and the like, where an artificial lens has to be inserted into the eye, the surgeon may wish to impose a degree of astigmatism when suturing the eye.

The degree of imposed astigmastism will vary from case to case and surgeon to surgeon, but will be of such an amount that the surgeon knows or believes will be relieved in due course to allow the eye to return to perfect ovality.

Heretofore easy and accurate methods for ascertaining how the tension in the sutures affects the circularity of the cornea and therefore the amount of tension a surgeon has to apply to the sutures to achieve a desired level of self correcting astigmatism, have not existed.

OBJECTS OF THE INVENTION

It is an object of the invention to provide a method and apparatus whereby it is possible, during a surgical operation, for the surgeon accurately to ascertain the effect which the tension in the sutures is having on circularity of the cornea, and thus by varying the tension allow the cornea to remain circular (in front view) or impose a slight ovality which he may decide is appropriate.

According to one aspect of the invention there is provided apparatus for use in ocular surgery comprising an eye piece and an objective lens for examining microscopically an object such as the cornea of the eye characterised in the provision of light means for directing a ring of light onto the cornea and arranged such that the cornea will reflect the ring for viewing through the eye piece in the focal plane of said objective lens, and means for determining the shape of said reflected ring and thereby the degree of corneal astigmatism of the eye.

Preferably the light means is in the form of a hollow ring provided with a plurality of annularly spaced light emitters.

Conveniently the light emitters are in the form of light emitting diodes (LED's) closely spaced around the ring so that the image reflected by the corneal surface of the eye is a substantially continuous ring.

Each LED is preferably circular in shape and may have a diameter of between 2 mm and 6 mm, and conveniently 5 mm. The LED's are preferably red in colour to contrast against the black pupillary aperture.

The light means preferably is provided with its own power source, conveniently a battery, for providing the power for the light emitting members thereof. A battery compartment or holder may be provided to accommodate the battery.

The means provided in the apparatus for determining the shape of the reflected ray in the arrangement defined above, is adapted to test whether the reflected ring is circular and if not the degree of non-circularity of the reflected ring. It may incorporate measuring means for measuring vertical and horizontal diameters of the image of the reflected ring of light.

Such measuring means preferably comprises a marker mounted in the eye piece and that is movable therein from a first position in which it is contiguous with one part of the reflected image and a second position at which it is contiguous to a diametrically opposite part of the reflected image, and means for determining the distance moved by the marker between the first and second position.

The measuring means further comprises means whereby the marker can make the same measurements along a diameter at 90° to the first mentioned diameter.

The adjusting means preferably comprises manually movable means such as an operating knob.

The marker may be a needle point or it may be a device carrying a line. Preferably the means for determining the distance moved by the needle is a micrometer, conveniently an electronic micrometer. Conveniently a digital read out of the distance moved by the marker is given.

The measuring means may alternatively comprise markings inserted in the or one of the eye pieces. Preferably, the calibrations or markings comprise an illuminated graticule in the eye piece which can be seen when an operator looks through the eye piece. There may be vertical and horizontal calibrations in the eye piece.

The determining means may also comprise comparator means. The comparator may be a printed sheet which the surgeon will be able to examine separately but preferably the comparator means comprises one or more items which may be placed into a separate eye piece of the apparatus for comparison with a reflected image.

Each eye piece may include a light member to illuminate the interior thereof so that the marker or graticule on the one hand and/or the comparator on the other hand (as the case may be) therein can be easily seen. The light member is preferably a nuclear light source in the eye piece. It may alternatively be a small globe in the eye piece and the globe may have a separate power source, for example, a battery, or it may be powered by the power supply to the microscope, if any.

According to another aspect of the invention there is provided apparatus for use with an ocular microscope comprising a support and means for mounting the support to the microscope characterised in that the support is provided with light means for directing a circular ring of light onto a cornea during ocular surgery so that the anterior convex cornea surface of the cornea will reflect the ring of light in such a way that any distortion thereof may be observed through the microscope.

Preferably the support is in the form of a ring provided on an annular surface thereof with a plurality of spaced lighting members, advantageously in the form of light emitting diodes (LED's).

According to a still further aspect of the invention there is provided an eyepiece for a microscope for determining the sphericity of the corneal surface of the eye, characterised in that the eyepiece is provided with means for examining the shape of the image of a ring of light focussed on said corneal surface, with preferred means for providing in the same field of view comparison rings of varying or adjustable eccentricity simultaneously viewed upon the light-ring image from the cornea.

According to a sill further aspect of the invention and in its preferred form, there is provided a method of monitoring the deviation of the curvature of the anterior surface of a cornea from substantially spherical shape as for the purpose of measuring corneal astigmatism or controlling corneal stretching and the like, that comprises producing a light reflected ring from a cornea anterior surface of diameter less than that of the cornea and viewing the same, the viewed ring varying from substantially circular shape for a spherical anterior surface cornea to successive degrees of elliptical eccentricity for successive degrees of astigmatism or deviation from spherical shape, viewing in the same field of view as the viewed reflected ring substantially circular ring disposed in a plane, effectively rotating the plane of the ring about a transverse axis of the ring to present the ring to said viewing as successive ellipses of successively varying eccentricity, and controlling the effective rotation to achieve superposition or concentricity with the particular elliptical ring of light reflected from the cornea, the amount of effective rotation being a measure of the degree of corneal astigmatism.

BRIEF DESCRIPTION OF THE DRAWINGS

Other features and advantages will become apparent from the following description of preferred embodiments of the invention taken with reference to the accompanying schematic drawings wherein.

BEST MODES OF CARRYING OUT THE INVENTION

Figure 1:
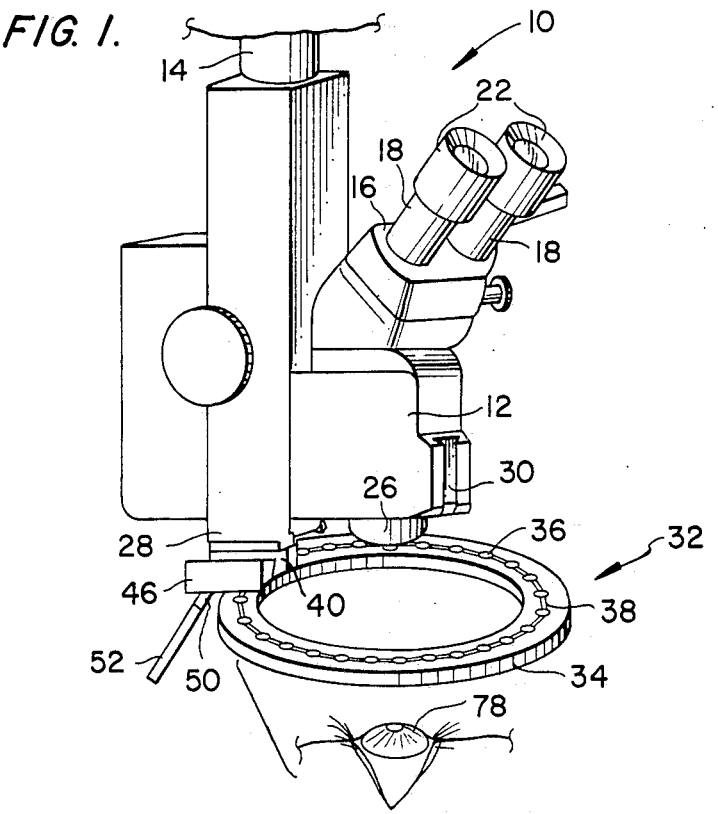
FIG. 1 is a perspective view of a microscope for use in ocular surgery according to the invention.
Figure 2:
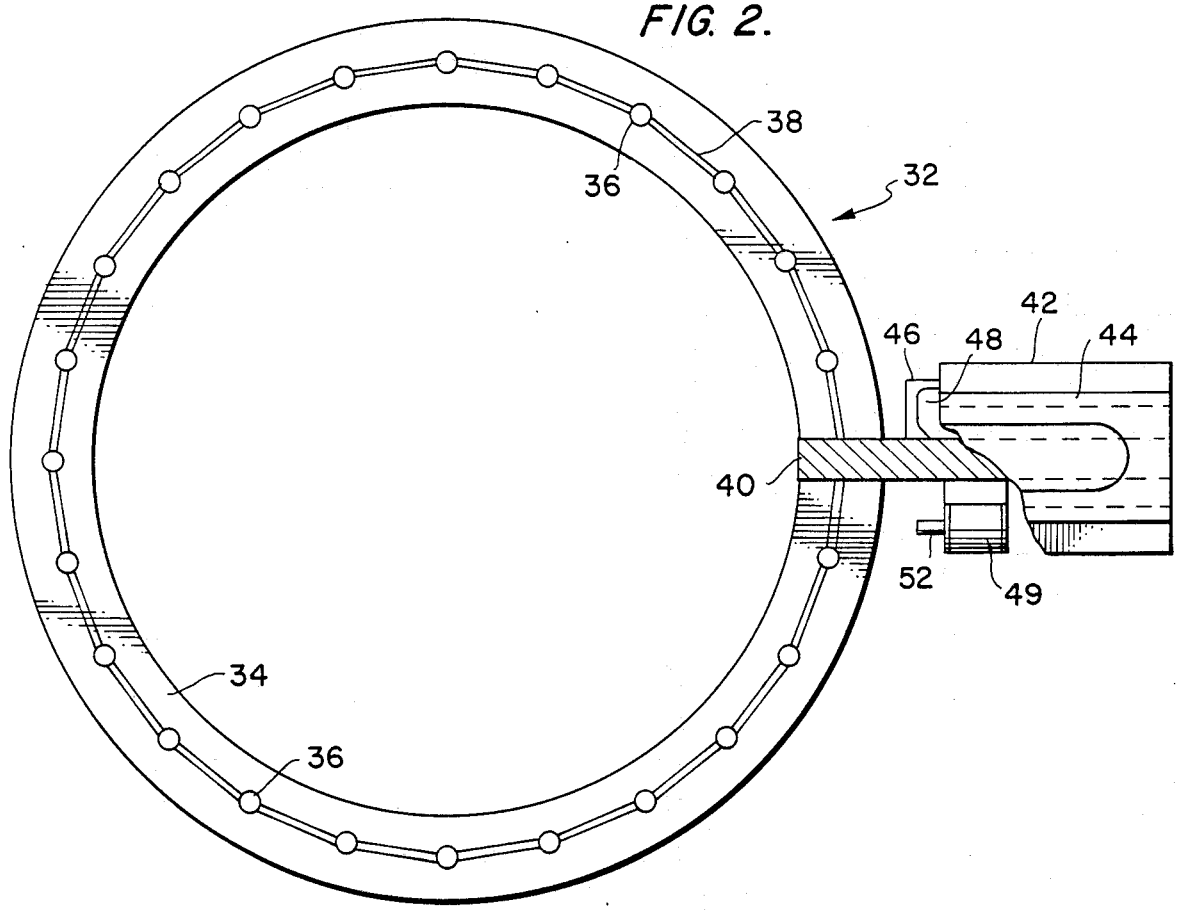
FIG. 2 is a plan view partially in section of the device for providing a ring of light for directing onto the coneal surface of an eye, and for attachment to the microscope of FIG. 1.

Referring now to FIG. 1 of the drawings, there is shown a binocular operating microscope 10. The microscope 10 comprises a body 12 which is supported by a suitable carrier means indicated at 14. Attached to the upper surface 16 of the body 12 there are two tubular pieces 18 which each slidably receive an eye piece 22. The lower end of the body 12 carries a single objective lens 26. A horizontal dove-tail receptor 28 is provided below the body 12 and a vertical dove-tail receptor 30 is provided on the side of the body. As thus far described, the microscope is conventional.

An illuminating member 32 is located about the objective lens 26. The illuminating member 32 comprises a hollow aluminium ring 34. A plurality of equispaced light emitting diodes (LED's) 36 are carried by the ring with their light emitting portions projecting through the lower surface of the ring 34. A pair of connecting wires 38 connects the rear of each of the LED's 36.

Brazed to the upper side of the ring 34 is a vertical aluminium plate 40 that carries a horizontal member 42 on which is formed a male dove-tail member 44.

The vertical plate 40 also carries a battery container 46 in which is received a dry cell battery 48. A switch 49 is mounted on the plate 40 and has a switch lever 50. The battery 48 is connected to the connecting wires 38 and hence to the LED's.

A removable aluminium sheet 52 fits over the switch lever 50. This sheath 52 can be sterilized in an autoclave so that the surgeon can operate the switch unit during an operation.

It will be seen that the illuminating means comprises a totally self-contained unit that is separate from the microscope and can be attached thereto with ease using the conventional carrying means (the dove-tail unit) normally provided on the microscope.

Figure 3:
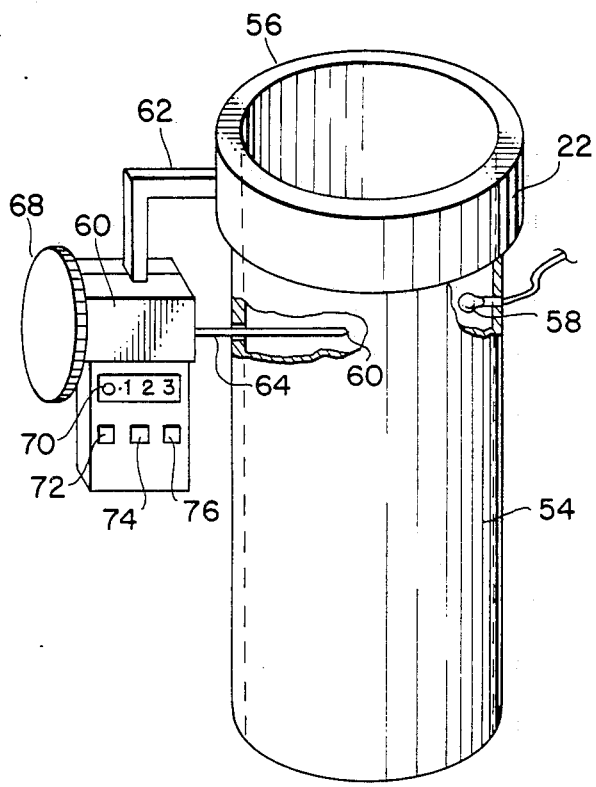
FIG. 3 is a perspective view of an eye piece of the microscope of FIG. 1 provided with means for analysing the shape of the image of the ring of light reflected from the corneal surface of the eye.

Reference is now made to FIG. 3 which is a perspective view of one of the two eye pieces 22. As is conventional the eye piece comprises a cylinder 54 having a peripheral collar 56 at its upper end. The cylinder 54 incorporates suitable lenses (not shown) in conventional manner. A light source 58 is provided in the cylinder 54.

A measuring device is provided for the eye piece. This measuring device (which is not shown in FIG. 1) comprises a digital electronic micrometer 60 that is supported by a clamp 62 secured to the cylinder 54. The micrometer 60 carries, outside the cylinder 54, a needle 64 which projects into the cylinder and which has a pointed end 66 which is viewed superposed upon the illuminated-ring corneal image.

An operating knob 68 is provided for the micrometer. This knob 68 may be covered by a sterilizable cover to permit the surgeon to handle it during an operation.

The micrometer 60 has a digital display unit 70 on which the distance of the pointed end 66 from a datum point can be read off. The display unit 70 has an on/off switch 72, a set switch 74 by means of which the display can be set to zero, and a conversion switch 76 by means of which a readout can be converted from inches to centimeters or vice versa.

In use, during an operation, the distance between the microscope 10 and the eye 78 which is being operated upon is adjusted depending upon the focal length and strength of the objective lens 26 but in any case at such a position that the surgeon can comfortably get his hands under the illuminating member 32 to operate on the eye.

When the surgeon wishes to examine the eye to ascertain the amount of distortion of the cornea, he switches on the switching unit thus energising the LED's 36 on the lower surface of the ring 34. The light given off by the LED's 36, which is preferably directed or focussed convergingly inward along the microscope for efficient use of the emitted light, is reflected from the anterior convex corneal surface of the eye which acts in effect as a convex mirror. The horizontal diameter of the reflected image is measured and then the vertical diameter is measured. The measurements are then compared and the difference, if any, provides an indication of the degree of astigmatism in a particular eye.

Figure 4:
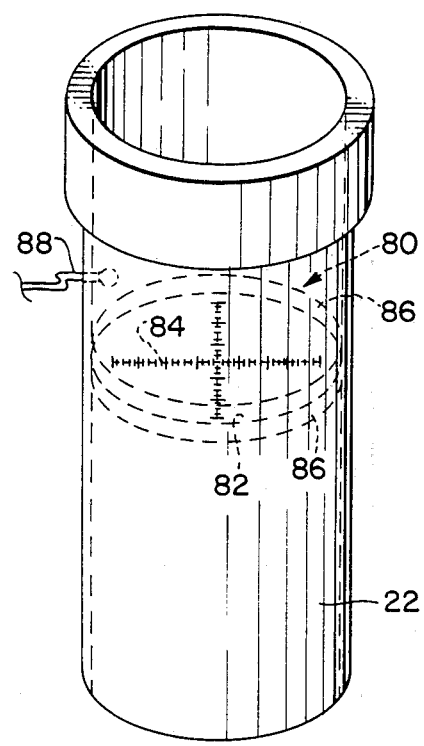
FIG. 4 is a perspective view of an eye piece of the microscope of FIG. 1, provided with an alternative means for analysing the shape of the image of the reflected ring of light from the corneal surface of the eye.

As an alternative to the arrangement above described, the eye piece 22 incorporates a graticule 80 as shown in FIG. 4. The graticule 80 comprises a transparent sheet of material 82 having calibrations 84 thereon in both the vertical and horizontal axes. The transparent sheet 82 is held in position within the eye piece by being sandwiched between two glass sheets 86.

A light 88 which is connected to a source of power (not shown) is provided in the eye piece 22a to illuminate the graticule 80 thereby assisting the operator in seeing the calibrations 84 of the graticule 80 superimposed on the light-ring image from the cornea.

In yet another alternative, there is provided a comparator sheet (not shown) which the surgeon can place close to the microscope so that after viewing the reflected image, he can compare this with the comparator. If desired, the comparator may be incorporated in the eye piece itself for superposition on the reflected light ring from the corneal.

Figure 5:
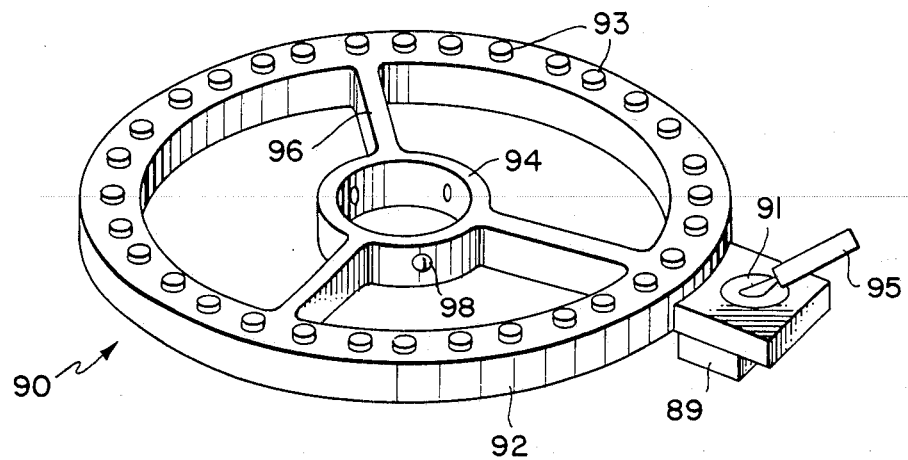
FIG. 5 is a perspective view of an alternative arrangement of the illuminating member of FIG. 2.

Reference is now made to FIG. 5 wherein is shown illustrated the underside of a modified illuminating member 90. The illuminating member 90 comprises an aluminium ring or annulus 92 similar to ring 32 and carrying high intensity red LED's 93. The ring 92 has a central apertured boss 94 to which it is connected by three narrow equispaced spokes 96. Three clamping screws 98 pass through the boss 94 for clamping this ring on to the objective lens 26 of the microscope. The illuminating member 90 carries a battery pack 89 with a battery and a switching unit 91 with a switch lever 95 covered by an aluminium sheath. The illuminating member 90 is a self-contained unit that can easily be fitted to a conventional microscope.

The ring 34 or 92 may be replaced by a completed disc with the LED's provided on the annular area at the periphery of the disc, preferably each focused inwardly to converge the light onto the cornea. A difficulty with such a disc is that it will obscure or interrupt (a) the vision of the surgeon when not using the microscope or (b) the assistant's microscope vision.

Figure 6:
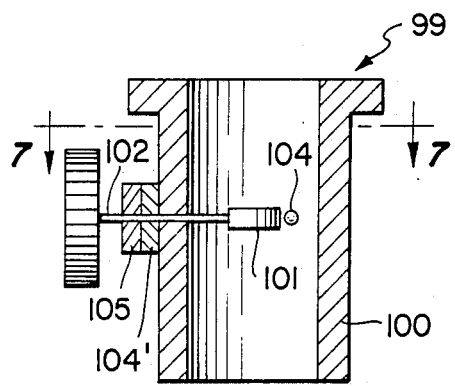
FIG. 6 is a detailed vertical section through an eye piece of the apparatus of FIG. 1, provided with an alternative means for analysing the image of the reflected ring of light from the cornea of the eye during ocular surgery.

Referring now to FIG. 6 there is shown a modified eye piece 99 for the microscope forming part of the apparatus of the invention as shown in FIG. 1. The eye piece 99, as is normal, comprises an elongated barrel 100 of about 20 mm internal diameter. Located at the focal plane of the lens of the eye piece, is a datum disc 101. This disc 101 comprises transparent material such as glass. It is about 4 mm in diameter. The disc 101 is carried by a rod 102 which is coincident with an extension of a diameter of the disc, which diameter is normal to the axis of the barrel 100.

Etched on to the surface of the disc 101 is a marking 103 (see FIG. 7) in the form of a circle or ring to be used for comparison in the same field of view with the light-reflected ring imaged in the ocular from the anterior surface of the cornea. Additional markings which are concentric therewith may also be etched into the surface of the disc 101. A nuclear or small lateral light source 104 is attached to the disc 101 to illuminate the markings.

The rod 102 extends through the wall of the barrel 100. Outside the barrel wall, the rod 102 passes through a large boss 104' fixed to the barrel wall inside which ring the rod carries a similar size ring 105. Beyond the ring 105, the rod 102 carries a knob whereby it, the rod 102, and with it the datum disc may be rotated about the said diameter. The two rings 104' and 105 have markings to indicate how much the rod 102 and the datum disc 101 with its comparison ring marking 103 have been rotated from the plane normal to the barrel axis.

This position of the disc 101 is hereinafter called the "zero position" of the disc 101.

On rotation of the plane of the datum disc 101 with its marked ring 103 about the transverse axis by rod 102 the ring takes the shape of a series of comparison rings ranging from circular to successively varying oval or elliptical eccentricities (sometimes referred to herein for convenience as "an oval"). The greater the degree of rotation of the disc 101 from the zero position, the greater the apparent ovality of the ring figure 103 formed by the markings and viewed superposed upon the LED-illuminated corneal ring image. It will be seen that the relationship of the ratio of the major and minor axes or eccentricity of the oval ring 103 relative to the angle of the disc out of the zero position will be determined by the cosine angle. It will also be appreciated that astigmatism of the cornea of an eye causes the light from the circular light source to be reflected thereby in the form of an oval or ellipse, the reflected ring of light from the anterior convex surface of the cornea being of diameter less than that of the cornea (preferably of pupil diameter or less) and the oval deviation from spherical shape representing successive degrees of astigmatism. By adjusting the angle of the disc 101 so that the apparent figure formed by the comparison ring markings 103 is congruent and superposed with that of the reflected light ring from the cornea, and then by reading off the angle from the rings 104' and 105, the surgeon can determine the degree astigmatism of the eye. Thus successive degrees of elliptical eccentricity of the ring 103 corresponding to successive degrees of astigmatism or oval deviation from spherical shape of the cornea are viewable, and matchable by superposition or concentricity with the actual image of the ring-illuminated cornea appearing in the ocular or eyepiece. For the convenience of the surgeon, the markings on the rings 104' and 105 are indicated in diopters of astigmatism.

Figure 8:
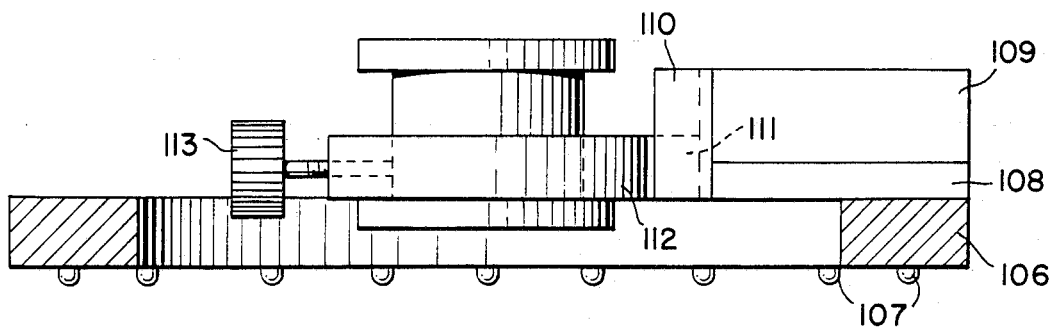
FIG. 8 is a side view, partially in section of a modified form of the device for directing a ring of light onto the corneal surface of the eye, of the apparatus of FIG. 1.

Referring now to FIG. 8 there is shown an aluminum ring 106 carrying a plurality of high intensity LED's 107 for providing a ring of light, again preferably converged along the axis of the microscope. Mounted on the upper surface of the ring 106 there is a radial plate 108 carrying a power source 109 for the LED's being a battery together with the switch therefor. At its inner side the plate 108 is provided with a female member 110 of a dove-tail joint. A male member 111 is carried on an adaptor 112 which surrounds the object lens and clamped thereto by a clamping member 113.

It will be understood that the apparatus of the invention has particular application in use in operations such as the cataract operations where an artificial lens is inserted into the eye and where the surgeon may wish to impose a degree of astigmatism into the eye when suturing the eye. The degree of imposed astigmatism will vary from case to case (and surgeon to surgeon) but will be of such an amount that the surgeon knows or believes will be relieved in due course to allow the eye to return to perfect ovality.

All items that the surgeon will touch during the operation should be covered by a removable cover which is capable of being sterilized before each operation.

Figure 7:
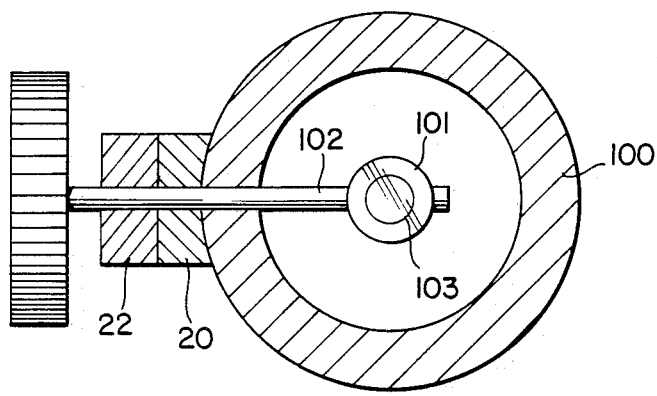
FIG. 7 is an enlarged section on line 77 of FIG. 6.

The constructional details hereinbefore described and illustrated in FIGS. 6 to 8 of the accompanying drawings may be readily modified. For example, the ring marking on the datum disc 101 may be replaced by an actual annular ring 103 which is similarly mounted on the end of the diameteral rod 102 of FIG. 7. With such a preferred arrangement, the inside diameter of the ring 103 must be greater than the reflected ring of light reflected from the cornea as simultaneously viewed in the ocular by the surgeon. The transverse rotation of the ring 103 again will vary the apparent eccentricity of the same as viewed superposed on the light-ring reflected image from the cornea.

Additionally means may be provided for locking the dove-tail members 30 and 40 at different axial locations so that the illuminating ring 30 can be moved toward and away from the eye. Thus the size of the reflected ring can be adjusted to correpond more closely to the size of the iris. Electronic or optical ring-presenting substitutes for a physical rotatable ring 103 may also be projected in the ocular viewing region, again viewed as superposed on the light-ring illuminated cornea, such as, for example, small cathode-ray tube Lissajou figures reflected, refracted on projected in the ocular viewing path, as upon a transparent disc like 103.

The alternative form of measuring means as described above with reference to FIGS. 6 through 8 is calibrated in diopters of non-circularity. Thus for example if the datum means has rotated 70° from the normal, then the ovality of the circular-elliptical ring as viewed would correspond to 2 diopters of astigmatism.

It will be appreciated that the present invention is not limited to the precise constructional details hereinbefore described and illustrated in the accompanying drawings and modifications may be made thereto falling within the purview of one skilled in the art but within the scope of the invention as defined in the following claims.

What is claimed is:

1. A method of monitoring the deviation of the curvature of the anterior surface of a cornea from substantially spherical shape as for the purpose of measuring corneal astigmatism or controlling corneal stretching and the like, that comprises producing a light reflected ring from the cornea anterior surface or diameter less than that of the cornea and viewing the same, the viewed ring varying from substantially circular shape for a spherical anterior surface cornea to successive degrees of elliptical eccentricity for successive degrees of astigmatism or deviation from spherical shape; viewing in the same field of view as the viewed reflected ring of light a substantially circular comparison ring disposed in a plane; effectively rotating the plane of the comparison ring about a transverse axis of the comparison ring to present the comparison ring to said viewing as successive ellipses of successively varying eccentricity; and controlling the effective rotation to achieve superposition or concentricity with the particular elliptical ring of light reflected from the cornea, the amount of effective rotation being a measure of the degree of corneal astigmatism.

2. A method as claimed in claim 1 in which the reflected ring is of pupil diameter or less.

3. A method of monitoring the deviation of the curvature of the anterior surface of a cornea from substantially spherical shape, as for the purpose of measuring corneal astigmatism or controlling corneal stretching and the like, that comprises, producing a reflected ring of light of diameter less than that of the cornea from the anterior convex surface of the cornea and viewing the same, the ring varying from substantially circular shape for a spherical anterior surface of the cornea to successive degrees of elliptical eccentricity for successive degrees of astigmatism or oval deviation from spherical shape; simultaneously viewing in the same field of view as the ring a series of comparison rings ranging from circular to successively varying elliptical eccentricities corresponding to successive degrees of corneal astigmatism; and selecting from the series during simultaneous viewing of the ring of light that comparison ring which achieves substantial superposition or concentricity with the ring of light, thereby indicating the degree of corneal astigmatism.

4. An eyepiece for a microscope used in ocular surgery comprising a cylindrical tube containing lens means for permitting an operator to view an image of a ring of light reflected from the surface of a cornea of an eye, said image having a degree of non-circularity which is dependent upon the degree of corneal astigmatism of the eye, and means for measuring the non-circularity of said image, said measuring means comprising a marker projecting radially through the wall of and into said tube for viewing by the operator, means mounted on the exterior of said tube for adjusting the amount of projection of said marker into said tube, whereby a portion of the marker may be visually aligned with opposite portions of said image, and means for indicating said amount of projection.

5. An eyepiece for a microscope used in ocular surgery comprising a cylindrical tube containing lens means for permitting an operator to view an image of a ring of light reflected from the surface of a cornea of an eye, said image having a degree of non-circularity which is dependent upon the degree of corneal astigmatism of the eye, and means for measuring the non-circularity of said image, said measuring means comprising a comparison ring disposed in said tube for viewing by said operator, said comparison ring having means for rotating it in the tube about a diameter of the comparison ring that is orthogonal to the axis of the tube such that the appearance of the comparison ring as viewed by the operator through the eyepiece can be varied from circular to different elliptical configurations for comparison with said image, and means for indicating the rotation of the comparison ring.

* * * * *